United States Patent [19]
Martin

[11] Patent Number: 5,053,023
[45] Date of Patent: Oct. 1, 1991

[54] CATHETER FOR PROLONGED ACCESS

[75] Inventor: Geoffrey S. Martin, Mississauga, Canada

[73] Assignee: Vas-Cath Incorporated, Canada

[21] Appl. No.: 662,329

[22] Filed: Feb. 25, 1991

Related U.S. Application Data

[63] Continuation of Ser. No. 261,970, Oct. 25, 1988, abandoned.

[51] Int. Cl.$^5$ ............................................. A61M 25/00
[52] U.S. Cl. ...................................................... 604/280
[58] Field of Search .................. 604/43, 160, 161, 175, 604/280, 283, 282

[56] References Cited

U.S. PATENT DOCUMENTS

| | | | |
|---|---|---|---|
| 4,417,888 | 11/1983 | Cosentino et al. | 604/175 |
| 4,596,559 | 6/1986 | Fleishhacker | 604/161 |
| 4,682,978 | 7/1987 | Martin | 604/283 |
| 4,692,141 | 9/1987 | Mahurkar | 604/43 |
| 4,772,268 | 9/1988 | Bates | 604/43 |
| 4,808,155 | 2/1989 | Mahurkar | 604/43 |

*Primary Examiner*—John D. Yasko
*Attorney, Agent, or Firm*—Rogers & Scott

[57] ABSTRACT

A flexible dual lumen catheter is provided for use especially in prolonged access. The catheter is especially used for such access in haemodialysis treatments and includes an elongate body having side-by-side lumens, distal and proximal ends, and one of the lumens being an intake lumen for receiving body fluid and other being a return lumen for leading fluid to the body. Connecting tubes are provided attached to the lumens and a tip is provided adjacent the distal end. The tip defines an intake opening spaced from the distal end of the body to provide access to the intake lumen and the return opening leads from the return lumen at the distal end of the body. The body has two portions, a distal portion adjacent the distal end for engagement within body tissue and a proximal portion extending between the connecting tubes and the distal portion, the distal portion having minimal rigidity for acceptance in the body tissue and the proximal portion having greater rigidity sufficient to minimize the risk of kinking during insertion and during normal use. A cuff is provided at the junction of the proximal and distal portions for attachment to the patient as blood clots in the cuff.

2 Claims, 2 Drawing Sheets

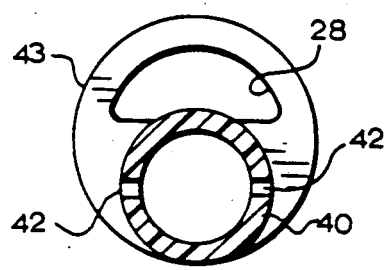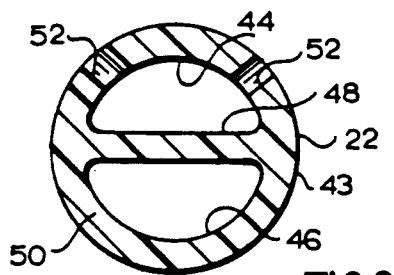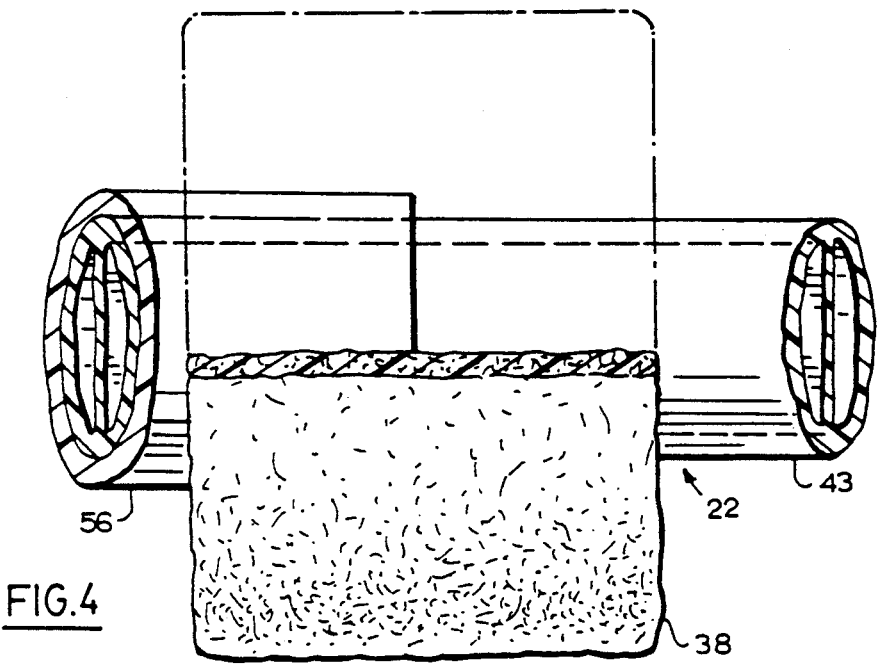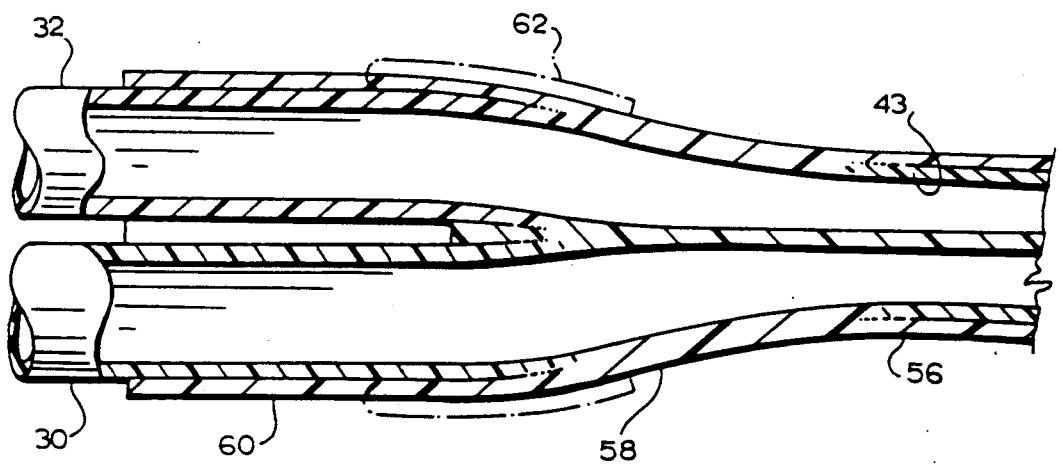

CATHETER FOR PROLONGED ACCESS

This application is a continuing application of application Ser. No. 07/261,970 filed on Oct. 25, 1988, now abandoned.

This invention relates to a dual lumen catheter and more particularly to such a catheter for longer term insertion into a vein of a patient for use in haemodialysis treatments.

Dual lumen catheters have been available for many years for a variety of medical purposes. It is only in recent years, however, that such catheters have been developed for use in procedures such as haemodialysis. The general form of dual lumen catheters goes back to as early as 1882 when Pfarre patented such a catheter in the United States under Serial No. 256,590. This patent teaches a flexible dual lumen catheter which is used primarily for cleaning and drainage of, for example, the baldder, rectum, stomach and ear. In this type of catheterization, the catheter is introduced into an existing body orifice without the use of a guiding structure.

More recently a dual lumen catheter was developed and patented by Blake et al under U.S. Pat. No. 3,634,924 for a different purpose. This 1972 patent teaches a dual lumen cardiac balloon catheter which is introduced into a large vein and the balloon inflated to control the flow in the vein. The catheter can in fact be placed by using the balloon as a "sail" to move with the blood from an ante-cubital or other peripheral vein through for example, the right heart chambers into the smaller radicals of the pulmonary artery where the catheter takes up its intended function. This patent is of interest because it explains how to make a tip for a dual lumen structure of the type which has become common for a variety of purposes including haemodialysis. The structure uses a plug to seal the end of one lumen and a wire which retains the shape of the other lumen during formation of the tip in a heated die.

The surgical cut-down technique was used universally for vascular catheter access and this technique can be traced back to the 17th century. It is only as recently as about 1952 that a new approach to vascular access was taught when an article was published by Dr. Sven Ivar Seldinger resulting from a presentation made at the Congress of the Northern Association of Medical Radiology at Helsinki in June of 1952. The technique is still current and essentially involves the use of a hollow needle to make an initial puncture, a very flexible wire is then entered through the needle and positioned in the vessel, and then the needle is withdrawn and a catheter is entered percutaneously over the wire which is itself later withdrawn. With this technique it became possible to make less traumatic vascular access and this has now become an accepted method of performing access in numerous medical techniques. One of these techniques which has been the subject of much research and development is haemodialysis.

Haemodialysis can be defined as the temporary removal of blood from a patient for the purpose of extracting or separating toxins therefrom and the return of the cleansed blood to the same patient. Haemodialysis is indicated in patients where renal impairment or failure exists, that is, in cases where the blood is not being properly or sufficiently cleansed, (particularly to remove water) by the kidneys.

In the case of chronic renal impairment or failure, haemodialysis has to be carried out on a repetitive basis. For example, in end stage kidney disease where transplantation of kidneys is not possible or for medical reasons is contra-indicated, the patient will have to be dialysed about 100 to 150 times per year. This can result in several thousand accesses to the blood stream to enable the active haemodialysis to be performed over the remaining life of the patient.

Towards the end of 1960, Dr. Stanley Shaldon and colleagues developed, in the Royal Free Hospital in London, England, a technique for haemodialysis by percutaneous catheterization of deep blood vessels, specifically the femoral artery and vein. The technique was described in an article published by Dr. Shaldon and his associates in the Oct. 14th, 1961 edition of The Lancet at Pages 857 to 859. Dr. Shaldon and his associates developed single lumen catheters having tapered tips for entry over a Seldinger wire to be used in haemodialysis. Subsequently, Dr. Shaldon began to insert single lumen inlet and outlet catheters in the femoral vein and this was reported in the British Medical Journal of June 19th, 1963. The purpose of providing both inlet and outlet catheters in the femoral vein was to explore the possibility of a "self-service" approach to dialysis. Dr. Shaldon was subsequently successful in doing this and patients were able to operate reasonably normally while carrying implanted catheters which could be connected to haemodialysis equipment periodically.

Some use was made of a flexible dual lumen catheter inserted by surgical cut-down as early as 1959. An example of such a catheter is that of McIntosh and colleagues which is described in the Journal of the American Medical Association of Feb. 21, 1959 at pages 137 to 138. In this publication, a form of dual lumen catheter is made of non-toxic vinyl plastic and described as being inserted by cut-down technique into the saphenous vein to the inferior vena cava.

The advantage of dual lumen catheters in haemodialysis is that only one vein access need be affected to establish continued dialysis of the blood, because one lumen serves as the conduit for blood flowing from the patient to the dialysis unit and the other lumen serves as a conduit for treated blood returning from the dialysis unit to the patient. This contrasts with prior systems where either two insertions were necessary to place the two catheters as was done by Dr. Shaldon, or a single catheter was used with a complicated dialysis machine which alternately removed blood and returned cleansed blood through a single lumen.

The success of Dr. Shaldon in placing catheters which remained in place for periodic haemodialysis caused further work to be done with different sites. Dr. Shaldon used the femoral vein and in about 1977 Dr. P.R. Uldall, in Toronto Western Hospital, Canada, began clinical testing of a subclavian catheter that would remain in place between dialysis treatments. An article describing this was published jointly by Dr. Uldall, the present inventor, and others in Dialysis and Transplantation, Volume 8, No. 10, in October 1979. Subsequently Dr. Uldall began experimenting with a coaxial dual lumen catheter for subclavian insertion and this resulted in Canadian Pat. No. 1,092,927 which issued on Jan. 6, 1981. Although this particular form of catheter has not achieved significant success in the market-place, it was the forerunner of dual lumen catheters implanted in the subclavian vein for periodic haemodialysis.

The next significant step in the development of a dual lumen catheter for haemodialysis is Canadian Pat. No. 1,150,122 to the present inventor. This catheter avoided the disadvantages of the Uldall structure and achieved some commercial success.

A subsequent development is shown in U.S. Pat. No. 4,451,252 also to the present inventor The structure shown in this patent utilizes the well known dual lumen configuration in which the lumens are arranged side-by-side separated by a diametric septum. The tip is formed to make it possible to enter a Seldinger wire through one of the lumens and to use this wire as a guide for inserting the catheter percutaneously. This type of structure is also shown in a European patent application to Edelman published under No. 0 079 719, and in U.S. Pat. Nos. 4,619,643, 4,583,968, 4,568,329, 4,543,087, 4,692,141, 4,568,329, and U.S. Design Pat. No. 272,651. All of these structures require quite stiff tips to facilitate dilating body tissue as the catheter is pushed over the wire and yet they must have flexible bodies to allow the catheter to follow the contour of the vein after placement. This has led to several approaches to manufacture a suitable tip on the body. Firstly the body material is chosen as a compromise between strength for end loading during insertion, flexibility after insertion, and resistance to kinking in the part of the catheter exposed after the catheter is in place. The tip is then formed from the same material and stiffened by concentrating the material, or a separate tip is added using stiffer material, or the tubing is first given a plug which stays in the tip after formation. Clearly the major design criteria are its need for strength to insert the catheter and the conflicting need for softness and flexibility after insertion.

The result of the design requirements for Seldinger placement is that the types of catheters satisfying these requirements are not suitable for prolonged placement. Catheters for this use must be extremely flexible to avoid stressing the vein and also to permit the catheter to move in the flow of blood to minimize the possibility of the catheter remaining in pressure contact with the wall of the vein at one spot for prolonged periods.

In summary, although there have been significant developments in the structures of dual lumen catheters, these structures are limited in their usefulness primarily because of the very design criteria inherent in making them suitable for placement by the Seldinger technique. The catheters are not suitable for prolonged placement.

The requirements for prolonged placement also lead to difficulties. While a soft and flexible catheter would be acceptable insofar as it follows vein contours and has minimal resistance to deflection in the flow of blood, such a catheter would be prone to kinking and flexing in the part positioned outside the patient. Also such flexibility would make handling during insertions impractical. As a result there is a tendency to compromise the design resulting in less than ideal characteristics for the tip and the portion of the catheter located in the vein.

It is among the objects of the present invention to provide a catheter for prolonged placement which mitigates the disadvantages of prior art structures. Accordingly, in one of its aspects, the invention provides a dual lumen catheter especially for use in prolonged access haemodialysis and which meets the requirements of flexibility and softness for prolonged access in a vein.

In another of its aspects, the invention provides such a catheter for prolonged access and having sufficient strength and rigidity in an outer portion which is not inserted to meet the requirements of a user to grip and manipulate the catheter and which will not kink in normal use.

In still another of its aspects, the invention provides a catheter which can be inserted in a vein for use in haemodialysis or similar treatments for prolonged periods and which will tend to move in the vein as blood flows around the catheter, at least during the treatments.

These and other aspects of the invention will be better understood with reference to the drawings and associated disclosure, in which:

FIG. 2 is a sectional end view on line 2—2 of FIG. 1 and drawn to a larger scale;

FIG. 3 is a view similar to FIG. 2 and drawn on line 3—3 of FIG. 1;

FIG. 4 is a sectional side view to the same scale as FIGS. 2 and 3 and drawn on line 4—4 of FIG. 1 to show a portion of the catheter at this location; and FIG. 5 is a sectional side view of the attachment between connecting tubes and the body of the catheter.

Figure 1:
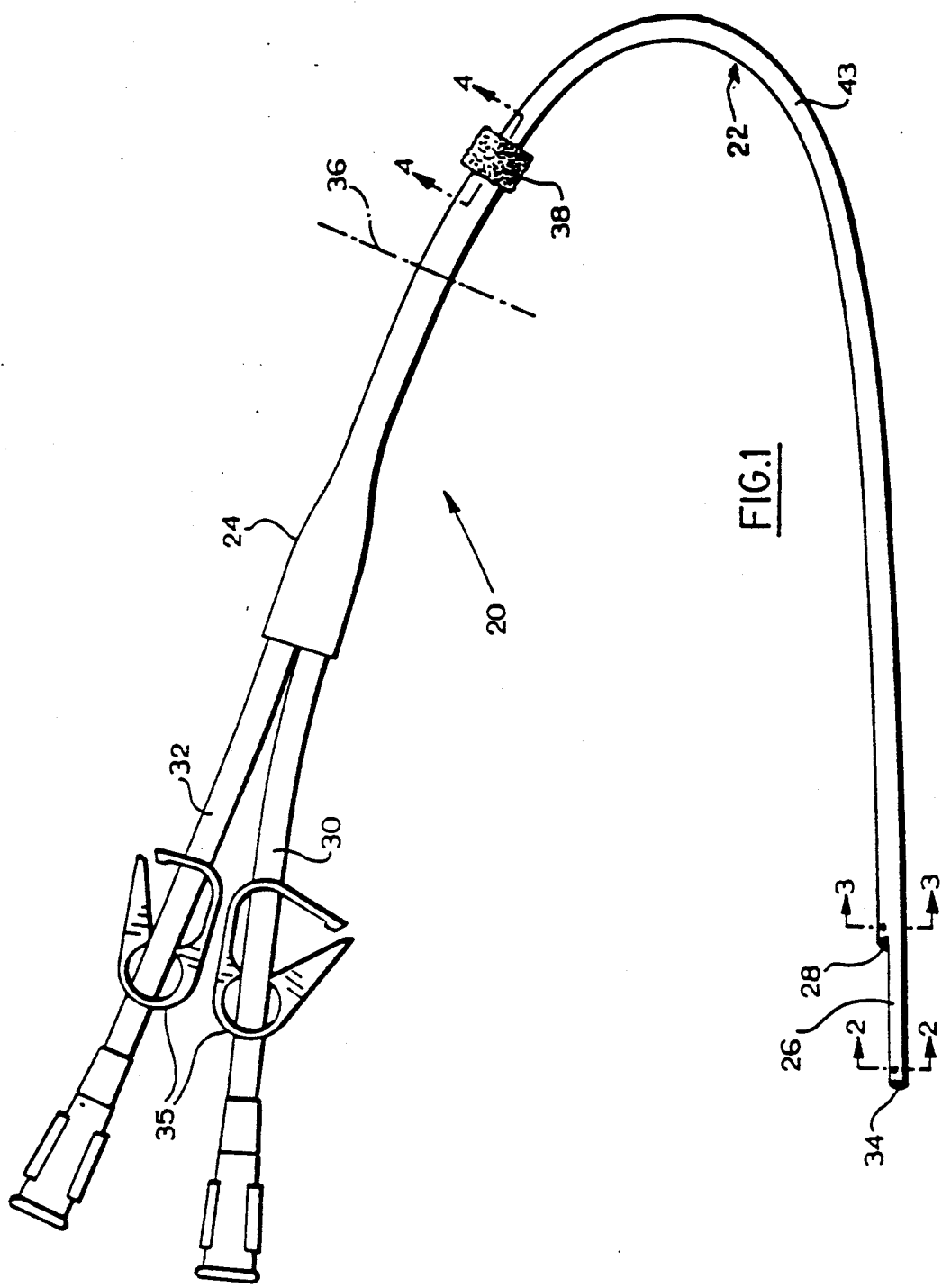
FIG. 1 is a side view of a catheter according to a preferred embodiment of the invention, with the distal end turned for a more perspective view of a tip on the catheter.

Reference is made firstly to FIG. 1 which illustrates an exemplary haemodialysis catheter 20 having an elongate main body 22 which extends from a connection 24 to a tip 26 and which contains intake and return lumens as will be described. In use, body fluid is withdrawn via an intake opening 28 at tip 26 into the intake lumen in the body 22 which is connected at the connection 24 to an intake tube 30 to withdraw blood. Treated blood is then returned through a return tube 32 via the return lumen which terminates at a return opening 34 at the distal end of the body 22.

Conventional clamps 35 are provided on the tubes 30, 32 which are of course flexible to permit use of these clamps. When engaged in a patient, the catheter would normally be engaged to a point indicated in the ghost outline by the chain-dotted outline 36 and a fibrous cuff 38 is provided to provide a seal where blood would clot in the cuff and seal the catheter to the patient.

The form of the tip immediately adjacent the distal end of the body 22 is better seen in FIG. 2. This sectional view shows a cylindrical tubular end portion 40 having a pair of side openings 42 to complement the return opening 34 (FIG. 1) and blending into the main body 22. In the background can be seen opening 28 which is simply the end of the intake lumen. The end portion 40 is formed from an extrusion the shape of which is seen in FIG. 3. This extrusion extends throughout the body 22 as will be explained, but is exposed only between the cuff 38 and the tip 26. The extrusion is in other words a first part of the body and will be designated by numeral 43. It will be seen that this part of the body is essentially cylindrical although within the practical lmitations of extruding, this shape may vary slightly.

The part 43 contains a D-shaped intake lumen 44 and a similarly shaped return lumen 46. These D-shaped lumens are separated by a septum 48 extending diametrically across the body between opposed locations on the inside of a side wall 50. The intake opening 28 is supplemented by a pair of side openings 52 adjacent the opening 28 and spaced circumferentially about the wall 50.

The section of the first part of the body shown in FIG. 3 actually extends throughout the length of the body 22 but is comple. ented by a stiffening second part extending between the proximal end of the body at the connector 24 and the cuff 38. It will be seen in FIG. 1 that this part of the body is wider than the part between the cuff 38 and the tip and the structure of this part will be described in more detail with reference to FIGS. 4 and 5.

Returning to FIG. 1, the tip 26 is formed by first cutting off a section of the body 43 corresponding to the intake lumen while leaving the septum and return lumen intact. A round mandrel is then placed in the portion in between openings 28 and 34 and heat is applied using a shaped die to permanently deform the material into the tubular cylindrical tip 26. The complementary openings 42 and 52 are then machined using a hollow drill.

As seen in FIG. 4, the body 22 actually consists of the first part 43 which extends throughout the length of the body and a second part 56 which fits snugly about the first part between the cuff 38 and the connector 24. With reference to FIG. 4, the cuff 38 serves also to cover the junction or exposed end of part 56 so that this end will not cause any interference in use. At the other end of the part 56, and as seen in FIG. 5, this part extends about the internal or first part 43 and, for reasons which will be explained, blends into this part at a junction portion 58. Similarly, the tubes 30, 32 also blend into this portion where they engage into the D-shaped lumens of the first part 43.

The arrangement shown in FIG. 5 has become typical in the art and is a modification to structures shown in earlier specifications, notably U.S. application Ser. No. 07/184,529. Initially the D-shaped lumens are flared to receive the tubes 30, 32 and the part 56 is shaped with a flare so that it will extend over the junction between the tube and the part 43. Generally the parts have the shape shown in FIG. 5. Next shaped heating tools are used in conjunction with shaped rods which are positioned inside the structure and the heat is applied externally under moderate pressure to cause some deformation and melting of the material so that the aforementioned blending takes place to attach the parts to one another and also to seal the joint. As a result, there is some of the part 56 extending over the tubes at a portion indicated by numeral 60. This portion is optional but does serve to protect the tubing during the heating process. After assembly, the portion can be turned back on itself as indicated in ghost outline and indicated by numeral 62 to further enhance the connection and strengthen the structure. However this is a optional step which is not essential to the operation of the catheter.

It will now be apparent that the body 22 is really in two portions as far as its characteristics are concerned. A distal portion between the cuff 38 and the tip is very flexible and after insertion is capable of taking up the contour of a vein and possibly moving in the vein as a result of blood flow and the forces applied in this flow. There is therefore less likelihood that the tip will stay in one position in a vein where it could, during use, cause stagnation points in the blood between the catheter and the vein. To help increase the likelihood of movement during use, the side openings 42 and 52 are provided in the structure as well as the axially orientated intake opening 28 and return opening 34.

The portion between the cuff 38 and the proximal end of the body 22 is stiffer because of the inclusion of the second part 54 of the body in external engagement around the first part 43 containing the D-shaped lumens. This increases the cross-sectional area and enhances the stiffness of the body and diminishes the likelihood of kinking caused by manipilation and accidental movement of the catheter outside the patient. The structure therefore overcomes the problems of providing a very flexible portion inside the patient and at the same time having sufficient rigidity outside the patient to minimize the risk of kinking.

The material used for the body of the catheter is typically soft medical grade polyurethane, with a Durometer A reading of 80. The portion of the body inserted in the patient is typically 11.5 French for haemodialysis and the insertion length 19 cm. The cuff is preferably of fibrous DACRON (trade mark of E. I. Dupont for a polyester material).

As mentioned previously, the catheter would often be inserted using conventional cut-down techniques. However, a modified Seldinger technique can also be used. In this case the Seldinger wire is used to lead a tubular guide into position in a vein and then the catheter is fed into the guide. It is then necessary to remove the guide by tearing or otherwise "peeling" the guide off the catheter. Such guides are common in the art.

The foregoing exemplary description teaches the invention in preferred form and is not to be used to limit the generality of the invention as claimed.

I claim:

1. In a catheter for use having an elongate body defining side-by-side generally D-shaped lumens and having distal and proximal ends, one of the lumens being an intake lumen for receiving body fluid and the other being a return lumen for leading fluid to the body, a pair of connecting tubes attached one to each of the lumens, the tubes being attached one to each of the intake and return lumens, and a tip adjacent the distal end and formed from the material of the body with the tip defining an intake opening spaced from the end of the body to provide access to the intake lumen and a return opening at the end of the body, the improvement in which the body is in two portions, a distal portion adjacent the distal end for enagement within body tissue, a proximal portion extending between the tubes and the distal portion, the distal portion having minimal rigidity for acceptance in the body tissue and the proximal portion having greater rigidity sufficient to minimize the risk of kinking during insertion and during normal use; and
   a fibrous cuff engaged about the body where the proximal and distal portions meet to provide a seal in use where blood would clot in the cuff to seal the catheter to a patient.

2. A catheter comprising:
   a generally cylindrical, elongate and very flexible first part having minimal rigidity for acceptance in body tissue and having distal and proximal ends and defining two D-shaped lumens, a first of the lumens being an intake lumen extending from an intake opening spaced from said distal end towards said proximal end and the other being a return lumen extending the full length of the first part and terminating at the distal end of the first part in a return opening;
   a tip formed adjacent the distal end of the first part, the tip extending from the return opening towards the intake opening and having a round cross-section;
   a pair of tubes;
   connection means coupling the tubes one to each of the lumens at said proximal end to provide for connection to the catheter to remove body fluid via the intake lumen and to return fluid to the body via the return lumen;

a tubular second part positioned snugly about a portion of the first part and extending from adjacent said proximal to an exposed end for enhancing the rigidity of the catheter where the catheter will be external to the patient after placement to minimize the risk of kinking during insertion and during normal use;

a fibrous cuff attached to the first and second parts to cover said exposed end and to provide a seal in use where blood would clot in the cuff to seal the catheter to a patient.

* * * * *